United States Patent
Lee et al.

(10) Patent No.: US 9,510,967 B2
(45) Date of Patent: Dec. 6, 2016

(54) ORTHOPEDIC DEVICE AND COMPONENTS THEREOF

(71) Applicant: Ossur hf, Reykjavik (IS)

(72) Inventors: Jane Lee, Fullerton, CA (US); Adam Dunn, Irvine, CA (US)

(73) Assignee: OSSUR HF, Reykjavik (IS)

( * ) Notice: Subject to any disclaimer, the term of this patent is extended or adjusted under 35 U.S.C. 154(b) by 712 days.

(21) Appl. No.: 13/913,780

(22) Filed: Jun. 10, 2013

(65) Prior Publication Data

US 2013/0331751 A1  Dec. 12, 2013

Related U.S. Application Data

(60) Provisional application No. 61/731,606, filed on Nov. 30, 2012, provisional application No. 61/657,482, filed on Jun. 8, 2012.

(51) Int. Cl.
*A61F 5/01* (2006.01)
*F16B 39/00* (2006.01)

(52) U.S. Cl.
CPC ............ *A61F 5/0125* (2013.01); *A61F 5/01* (2013.01); *A61F 2005/0158* (2013.01)

(58) Field of Classification Search
CPC .......... A61F 5/01; A61F 5/0125; F16B 5/025; F16B 5/0258; F16B 37/145
USPC .......... 24/200, 593.11, 593.1, 633; 411/338, 411/166; 602/16, 5, 20, 23, 26
See application file for complete search history.

(56) References Cited

U.S. PATENT DOCUMENTS

| | | |
|---|---|---|
| 49,305 A | 8/1865 | Ruggles |
| 243,605 A | 6/1881 | Ott |
| 932,177 A | 8/1909 | Roth |
| 1,927,061 A | 9/1933 | Chapman |
| 2,090,367 A | 8/1937 | Janes |
| 2,172,309 A * | 9/1939 | Langhammer .......... A41F 11/04 24/200 |
| 2,615,218 A | 10/1952 | Ross |
| 2,636,234 A | 4/1953 | Reiter |
| 2,928,153 A | 3/1960 | Reiter |

(Continued)

FOREIGN PATENT DOCUMENTS

| | | |
|---|---|---|
| CA | 2549987 A1 | 7/2005 |
| CN | 102307549 A | 1/2012 |

(Continued)

OTHER PUBLICATIONS

International Search Report from corresponding PCT Application No. PCT/US2013/044743, Sep. 5, 2013.

*Primary Examiner* — David E Sosnowski
*Assistant Examiner* — Jason W San
(74) *Attorney, Agent, or Firm* — Workman Nydegger (57) ABSTRACT

A strap tab assembly has a strap tab defining a substantially square-shaped locking hole located generally at a first end, and an elongated slot on a second end. The strap tab assembly includes a top cap defining a top cover, a square-shaped locking projection corresponding in shape to the locking hole, and a female portion forming a center channel and extending beyond and concentric with the locking projection. A bottom cap has a male portion adapted for being received in the center channel of the female portion to engage the top cap. The locking projection extends beyond the periphery of the female portion, and is configured and dimensioned to correspond to and engage an inner periphery of the locking hole.

12 Claims, 10 Drawing Sheets

(56) References Cited

U.S. PATENT DOCUMENTS

| | | | |
|---|---|---|---|
| 3,528,412 | A | 9/1970 | McDavid |
| 4,291,822 | A | 9/1981 | Simonds |
| 4,773,404 | A | 9/1988 | Townsend |
| 4,955,369 | A | 9/1990 | Bledsoe et al. |
| 5,086,760 | A * | 2/1992 | Neumann ............. A61F 5/0123 602/16 |
| 5,288,287 | A | 2/1994 | Castillo et al. |
| 5,292,303 | A | 3/1994 | Bastyr et al. |
| 5,383,845 | A | 1/1995 | Nebolon |
| 5,409,449 | A | 4/1995 | Nebolon |
| 5,458,565 | A | 10/1995 | Tillinghast, III et al. |
| 5,624,390 | A | 4/1997 | Van Dyne |
| 5,657,514 | A * | 8/1997 | Fabrizio ............... A44B 11/006 24/200 |
| 6,425,166 | B1 * | 7/2002 | Seligman ................ A61F 5/01 24/265 AL |
| 6,719,713 | B2 | 4/2004 | Mason |
| 6,845,548 | B1 | 1/2005 | Lin |
| 7,261,700 | B2 | 8/2007 | Verkade |
| 7,285,103 | B2 | 10/2007 | Nathanson |
| 7,507,215 | B2 | 3/2009 | Ryan |
| D637,942 | S | 5/2011 | Lee et al. |
| 2003/0176823 | A1 * | 9/2003 | Mason ..................... A61F 5/01 602/5 |
| 2003/0176824 | A1 * | 9/2003 | Mason ..................... A61F 5/01 602/12 |
| 2005/0148917 | A1 * | 7/2005 | Nathanson ............... A61F 5/01 602/23 |
| 2005/0222530 | A1 * | 10/2005 | Verkade ................ A61F 5/0123 602/26 |
| 2010/0331750 | A1 | 12/2010 | Ingimundarson |
| 2013/0060179 | A1 * | 3/2013 | Modglin .................. A61F 5/01 602/18 |
| 2013/0150761 | A1 * | 6/2013 | Romo ..................... A61F 5/01 602/16 |
| 2013/0331754 | A1 * | 12/2013 | Dunn ...................... A61F 5/01 602/16 |
| 2014/0308065 | A1 * | 10/2014 | Deharde ................ F16F 15/04 403/113 |
| 2015/0051528 | A1 * | 2/2015 | Gilbert .................... A61F 5/01 602/16 |
| 2016/0008157 | A1 * | 1/2016 | Brookover ............ A61F 5/0123 602/16 |
| 2016/0015546 | A1 * | 1/2016 | Knecht ................. A61F 5/0125 602/14 |

FOREIGN PATENT DOCUMENTS

| | | |
|---|---|---|
| WO | 03017890 | 3/2003 |
| WO | 2005097015 | 10/2005 |

* cited by examiner

ORTHOPEDIC DEVICE AND COMPONENTS THEREOF

TECHNICAL FIELD

The present disclosure relates to an improved strap tab assembly for connecting straps to various articles, including orthopedic devices such as knee brace frames.

BACKGROUND

Various types of orthopedic braces are available for individuals with musculoskeletal problems. Although conventional orthopedic braces embody a wide range of structures, they serve the similar purpose of supporting and stabilizing a joint when worn on the body of a user. When used in this manner, such braces may help prevent injuries from occurring in the first place. A brace can add support and stability to a healthy skeletal joint to reduce the risk of injury when the joint is subjected to undue stress. Alternatively, braces may help provide relief and restore functionality to an injured person by providing stabilizing support to a weakened skeletal joint to reinforce it and reduce the risk of sustaining further injury.

Many types of braces use straps for fastening to the individual. Such straps secure the brace to an individual's injured limb so the brace can apply force to the limb. Adjusting the tension in the strap affects the function, fit and comfort of the brace. The ability to increase the tension applied by the straps on the brace is very important because insufficient tension can prevent the brace from staying in place on the limb, and diminish its ability to stabilize or protect the limb. Too much tension, however, can restrict the individual's blood flow and make the brace very uncomfortable to wear. Many braces have support straps that may be tightened or loosened by shortening or lengthening the straps, respectively. This allows the user to adjust the fit of the brace to the limb and correspondingly adjust the support that the brace provides.

One type of brace that commonly uses fastening straps is a knee brace. Many knee braces include an upper member strapped to an individual's thigh, and a lower member strapped to an individual's calf to provide stabilization and protection to a knee joint. A hinge is used to connect the upper member to the lower member along the knee joint for maintaining the thigh and calf in proper alignment so both lateral displacement of the knee joint and hyperextension of the lower leg can be prevented. The straps used to secure the brace to the user may be attached via a strap tab. A variety of means exist for securing each strap tab to the brace, and all have their drawbacks.

Caps have been used to couple strap tabs to the frame of the brace. Conventional caps suffer from an assortment of shortcomings that limit their effectiveness as a connection device. For instance, many caps allow a strap tab to only be attached to an external portion of the brace frame. Such caps are bulky and significantly protrude outwardly from the surface of the brace once attached. The result is a brace frame with an undesirably thick profile at the locations where the strap tabs are attached. Such a thick profile increases the possibility that the strap tabs on the side of the brace frame will snag or catch onto something during use. Such a thick profile could increase the likelihood that a portion of the strap tab could contact a user and cause irritation when the brace is worn.

Another disadvantage of conventional caps is they do not allow the strap tabs to fully rotate relative to the brace upon which they are attached to. When the strap tabs are not provided with a full range of rotational motion, the straps used for securing the brace to a user cannot be precisely positioned. Usually such caps are rigidly secured to the brace frame, which does not permit the tabs to be adjusted. Any straps connected to such a tab are not adjustable for conforming to a desired shape of the user's body. Therefore it is an object of the present disclosure to provide a strap tab assembly fully rotatable and which can be adjusted according to the user's body and needs. Strap tabs that are permanently affixed to a brace frame are also undesirable since they do not permit rotation relative to the brace frame for adjusting the strap position. This is a significant problem since the straps on the brace must conform to the shape of the user to provide maximum comfort and effectiveness as described above.

Another goal of the present disclosure provides a strap tab that can be adjusted with ease. An undesired consequence of using a screw to attach a strap tab to the base frame is the screw is often overtightened, which makes rotating the tab overly difficult. A strap tab is sought that can be smoothly rotated relative to the frame upon which it is attached, but which is also sufficiently secured to the frame so it does not freely rotate without assistance from a user. The presence of screws can also increase discomfort for the user depending on where screw is located, and whether a portion of the screw protrudes from the frame when attached. It is important that the present disclosure does not make wearing a brace uncomfortable.

Many strap tabs that have tried to solve these problems lack the structural integrity for fastening a strap to the brace. Therefore it is another object of the present disclosure to provide a strap tab assembly adequately strong enough to withstand tension applied from the attached straps. Conventional connectors that comprise multiple pieces assembled together to create a loop-like structure have a diminished structural integrity. Using many pieces to create a connector is also cumbersome, and it is easy to lose them. These conventional connectors are not readily field-serviceable, and are difficult to adjust on the fly.

There exists a substantial need for an improved strap tab assembly for attaching to a brace frame for securing straps thereto. It is desirable that a strap tab has a minimal profile such that it is comfortable for the user. It is also desirable that the strap tab remains fully and easily rotatable relative to the brace frame, without its structural integrity being compromised. Finally, it is desirable that the strap tab is both aesthetically pleasing and inexpensive to manufacture. The present disclosure addresses all of these aforementioned needs.

SUMMARY

Under various embodiments described, a strap tab assembly is provided for securing a tightening strap to an orthopedic brace, such as a knee brace. The embodiments are provided for allowing full rotation of the connector relative to the brace. The strap tab of the present disclosure can be easily rotated as desired, but is also prevented from freely rotating when no external force is applied to it. A goal of the strap tab of the present disclosure allows for field-serviceability so it may be adjusted with ease by the user, even during use. The adjustability of the strap tabs allows the corresponding straps to be easily adjusted by the user for conforming to specific body parts.

Another goal of the present disclosure offers a strap tab with a low profile so it does not inhibit operation of the brace when attached thereto. A low profile will decrease the chance that the strap tab may snag a foreign object when the brace is worn. It is also beneficial that the strap tab assembly is sufficiently strong to support varying levels of tension applied by the straps when the brace is tightened to a user. Since the strap tabs of the present disclosure can be attached to either the internal or external surface of the brace frame as desired, they must do not make wearing the brace uncomfortable for the user.

Each strap tab can be on either the internal or external surface of the brace frame, and can also be secured to another corresponding strap tab on the opposite surface of the frame. In this embodiment, a single fastener secures the strap tabs to each other, such that the brace frame is positioned between each tab. This configuration allows the strap tabs to independently rotate relative to both each other and the brace frame, which helps the corresponding straps better conform to the shape of the user when the brace is worn. It also allows for extra straps to be used to better secure the brace to a user, or to provide a backup strap for the event that a first strap breaks.

In a first embodiment, the strap tab assembly has a strap tab defining a substantially square-shaped locking hole located generally at a first end, and an elongated slot on a second end. The strap tab assembly includes a top cap defining a top cover, a square-shaped locking projection corresponding in shape to the locking hole, and a female portion forming a center channel and extending beyond and concentric with the locking projection. A bottom cap has a male portion adapted for being received in the center channel of the female portion to engage the top cap. The locking projection extends beyond the periphery of the female portion, and is configured and dimensioned to correspond to and engage an inner periphery of the locking hole.

The center channel may axially extend through the female portion and the locking projection. The center channel may define a generally square-shaped profile, and the male portion has a generally square-shaped profile configured and dimensioned to mate with the profile of the center channel. The male portion defines a threaded cavity concentric with the square-shaped profile thereof.

A fastener may be used to secure the top and bottom caps to one another. In an embodiment, the top cover defines a recess for receiving the fastener and communicating with the center channel. The fastener may be arranged to be seated within the recess and extend into the center channel to engage the threaded cavity and secure the top cap to the bottom cap. The fastener may be flush with the top cover when secured to the bottom cap. The fastener may be rotatable independently relative to the top and bottom caps.

The top and bottom caps may be substantially flat, or have a shape that minimizes projection from the strap tab.

A washer may be located between the top and bottom caps. The washer may have a central opening through which the female portion is extendable. The washer preferably has a wave-like shape.

In a variation, the strap tab may define a recess concentric with the locking hole. The recess has a shape corresponding to the top cover. The top cover may be arranged flush against the strap tab within the recess.

The strap tab assembly may be used in combination with a frame element defining a hole through which the female portion extends and freely rotates within the hole. The frame may belong to an orthopedic device, and straps may be secured to the strap tab by the elongated slot. The strap tab assembly may be positioned on either side of the frame element.

A method for attaching the strap tab assembly to the frame element defining the hole includes the steps of connecting the strap tab defining a substantially square-shaped locking hole located generally at a first end to the frame element, providing the top cap defining a square-shaped locking projection corresponding in shape to the locking hole, and a female portion forming a center channel and extending beyond and concentric with the locking projection, and engaging the locking projection within the locking hole so as to prevent rotational movement of the top cap relative to the strap tab.

The method may include inserting a male portion of a bottom cap into a center channel defined by the female portion. The strap tab may define a recess along a first surface thereof. The method may include the step of placing the top cover within the recess of the strap tab.

These and other features, aspects, and advantages of the present disclosure will become better understood regarding the following description, appended claims, and accompanying drawings.

The drawing figures are not necessarily drawn to scale, but instead are drawn to provide a better understanding of the components thereof, and are not intended to be limiting in scope, but rather to provide exemplary illustrations. The figures illustrate exemplary embodiments of a strap tab assembly and the components, and in no way limit the structures or configurations of a strap tab assembly and components according to the present disclosure.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

The strap tab assembly described is configured for use with an orthopedic brace, such as a knee brace. It should be remembered, however, that the same concepts and methods described may be similarly used for other orthopedic devices and are not limited solely to the anatomical locations discussed.

General anatomical terms for the human body may be used for describing particular locations of the elements of the strap tab assembly in comparison to the human body.

The terms "medial" and "lateral" are relative terms used in reference to the human body. "Medial" is generally understood to indicate a location near the midsaggital plane or midline. Therefore, elements located near the midline are "medial" and those located further from the midline are "lateral." The terms "proximal" and "distal" refer to areas on the strap tab that correspond to a location relative to its point of attachment on a brace.

B. Embodiments of the Strap Tab Assembly

The following description refers to a strap tab assembly configured for securing a strap to the frame of an orthopedic brace, such as a knee brace. The features of this disclosure may apply to strap tabs for use with any type of orthopedic device that uses straps for securing the brace to a user. It should also be appreciated that the scope and aspects of the embodiments disclosed may apply to various other devices for which it is desirable to attach a strap thereto. In each embodiment, the strap tab assembly is attached to the brace in such a manner it maintains a full range of rotational motion relative to the brace.

Figure 1:
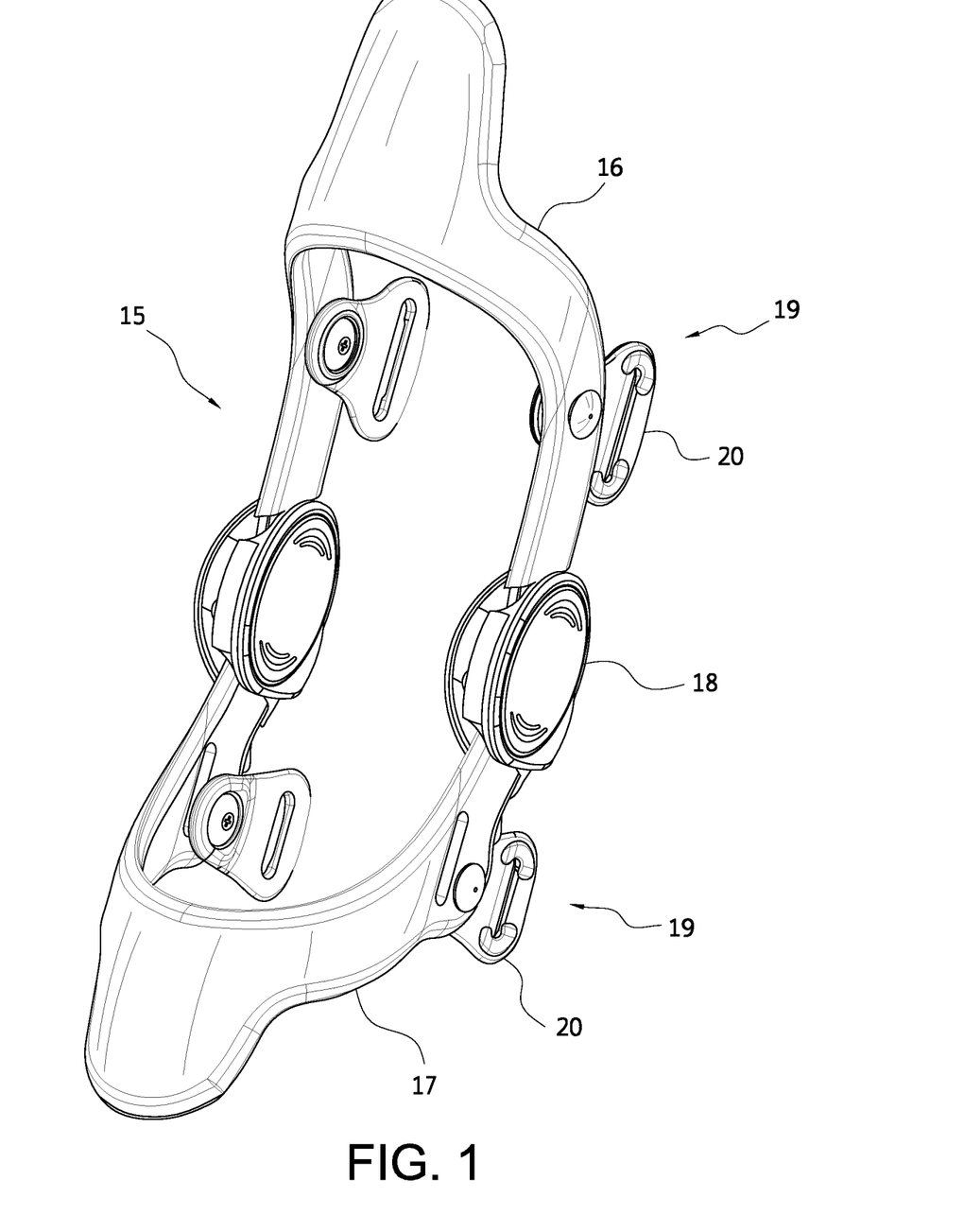
FIG. 1 is a perspective view of a knee brace utilizing multiple strap tabs according to an embodiment of the disclosure.
Figure 2:
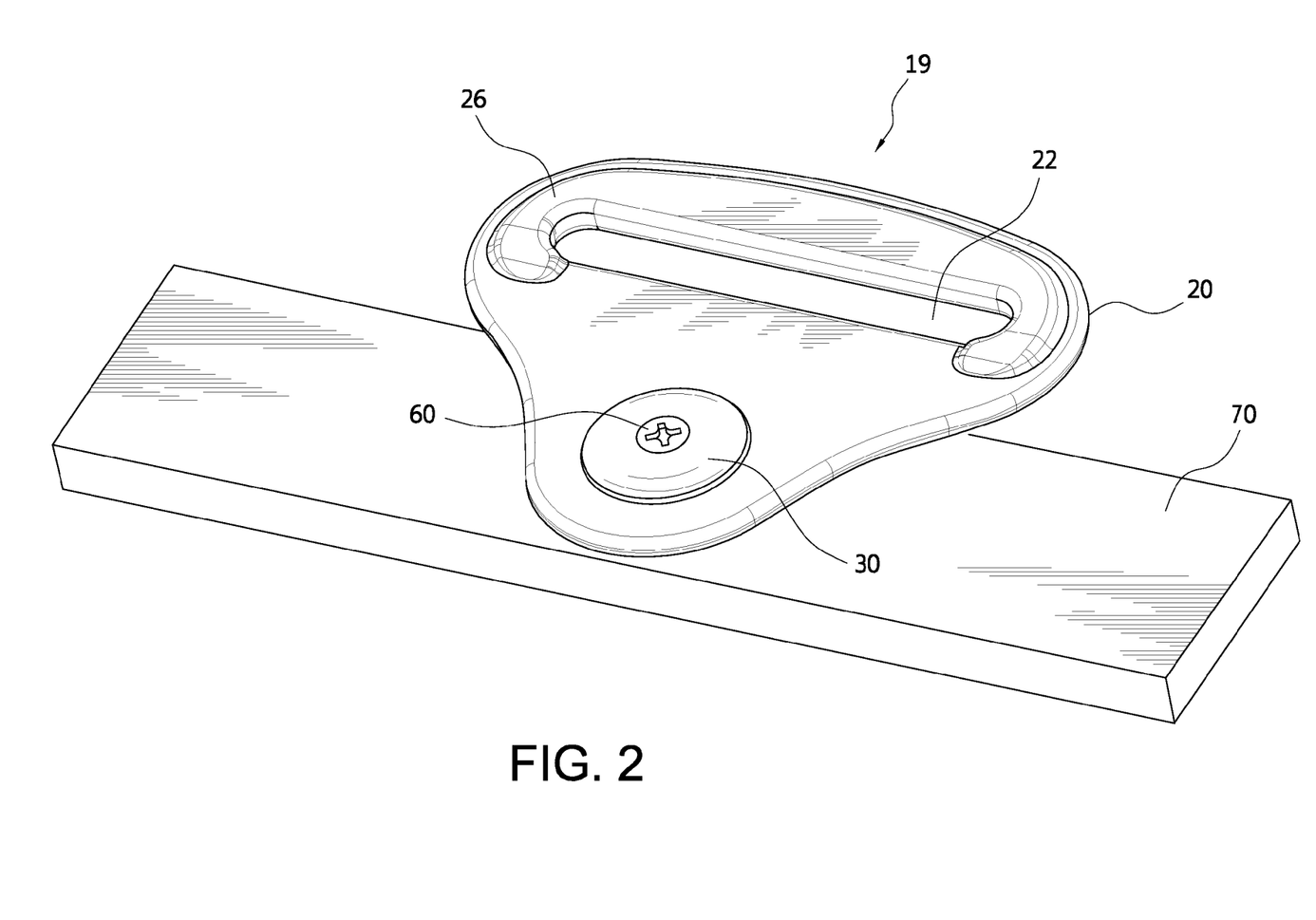
FIG. 2 is a perspective view of an embodiment of the strap tab assembly attached to a portion of a brace frame according to the disclosure.

Referring to FIG. 1, an example is shown of a knee brace 15 that uses an improved strap tab assembly 19 according to an embodiment of the present disclosure. This knee brace 15 has both upper and lower portions 16, 17 connected together via a hinge 18. These upper and lower portions are for attaching to a user's leg above and below the knee, respectively. The strap tab assembly 19 comprises a rotatable strap tab 20 that is removably connected to either of the medial and lateral sides, on either inner and outer surfaces of the upper and lower portions of the brace.

Each strap tab 20 is shown connected to the internal side of the brace frame such that it contacts a user's body when worn. It should be appreciated, however, that an advantage of the strap tab 20 of the present disclosure is it can be connected either to the internal or external side of the brace frame as desired. A strap is then inserted through an elongated slot 22 of each corresponding strap tab on the upper and lower portions of the brace, such that when tension applies to the strap, the brace is urged close against the user.

Turning to FIGS. 2-6, the strap tab assembly 19 further comprises a top cap 30, a bottom cap 40, a washer 50, and a fastener 60. The strap tab 20 is shown as a loop-shaped member, such as a D-ring. The distal end of the strap tab 20 is wider than its proximal end. It should be appreciated, however, that the shape and size of the strap tab 20 may take a variety of forms under the brace upon which it is attached to.

In the illustrated embodiment, the strap tab 20 is provided for connecting a strap (not shown) to a brace frame 70, such as a carbon frame. Such a strap connected to the brace frame 70 by a strap tab helps secure the brace to a user when worn. The strap tab 20 includes an elongated slot 22 for receiving a strap at its distal end. The strap tab 20 is adapted to accommodate many types of straps. An adjustable strap, such as one employing a hook and loop technique utilizing Velcro®, can fit through each elongated slot 22. When such straps are used on a knee brace, the tension applied to each strap tightens the brace against the user.

Still referring to the embodiment shown if FIGS. 2-6, both the top and bottom surface of the strap tab 20 is substantially flat to provide a low profile when attached to a brace frame 70. Either or both the top and bottom caps 30, 40 may have a substantially flat profile. Such a low profile provides extra comfort to a user when the strap tab 20 is attached to the internal side of a brace frame. This is because there is less irritation caused from the strap tab 20 pressing directly into the user's skin. A raised portion 26 may be provided adjacent the elongated slot 22 on one or both surfaces of the strap tab 20 to reinforce its structural integrity and protect it from the stress resulting from increased tension when each strap is fastened.

The strap tab 20 also includes a square-shaped locking hole 24 at its proximal end. This locking hole 24 allows the top cap 30 and bottom cap 40 to engage each other for rotatably attaching the strap tab 20 to a hole 72 in the brace frame 70. The top cap 30 includes a convex top cover 36 on one end that maintains a low profile relative to the strap tab 20 when attached thereto. The top cap 30 also includes a female portion 38 that has a substantially cylindrical exterior, and which is on the end opposite the top cover 36. A square-shaped locking projection 34 corresponding to the locking hole 24 is on the top cap 30 between the top cover 36 and the female portion 38. A non-threaded center channel 32 with a square cross-section axially extends throughout both the female portion 38 and the locking projection 34. Preferably the top cap 30 is made from a durable yet resilient material, such as plastic.

Figure 3:
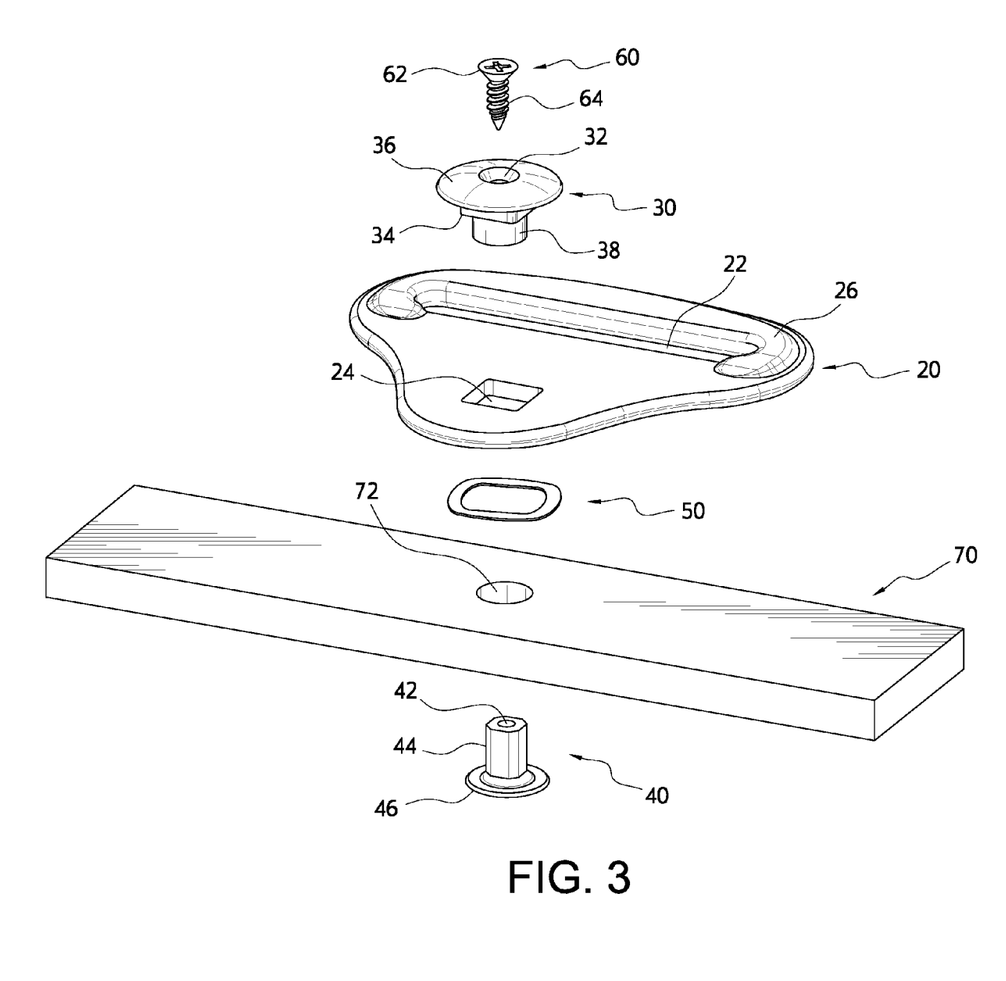
FIG. 3 is an exploded perspective view of strap tab assembly of FIG. 2.
Figure 4:
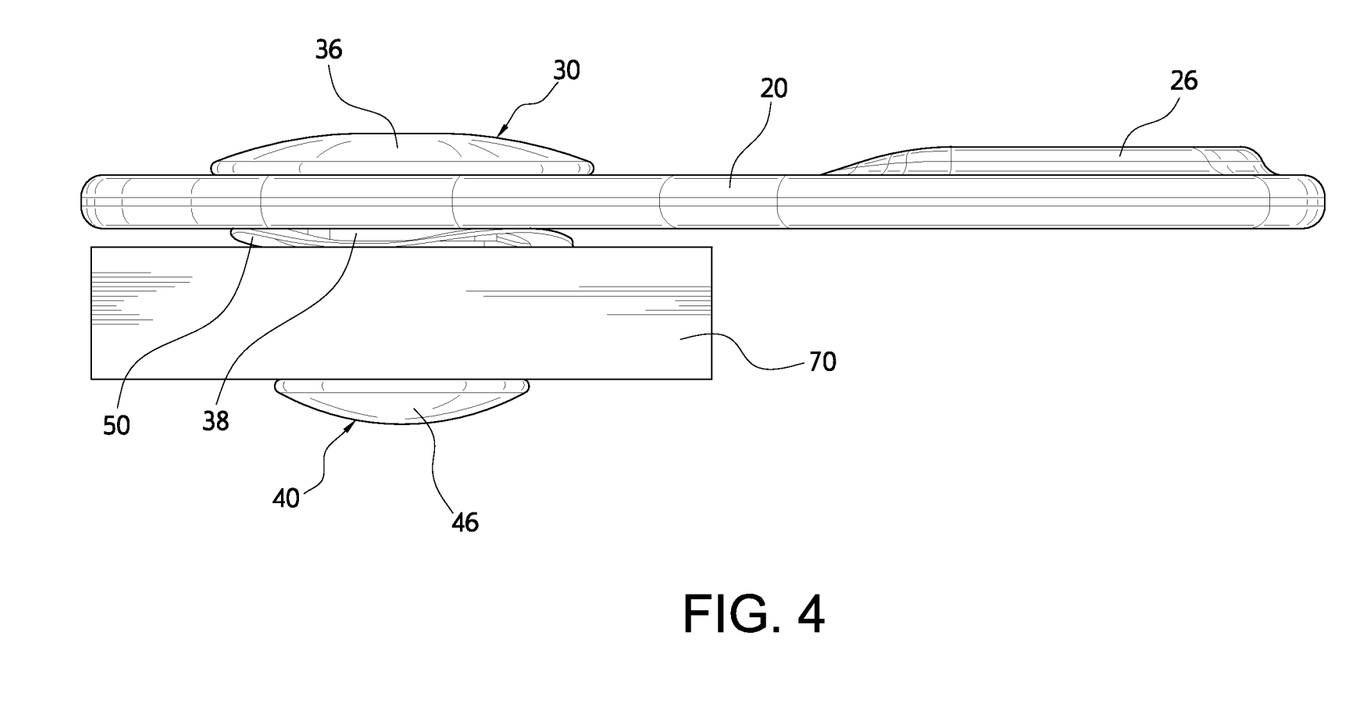
FIG. 4 is a side elevation view of the strap tab assembly of FIG. 2.
Figure 5:
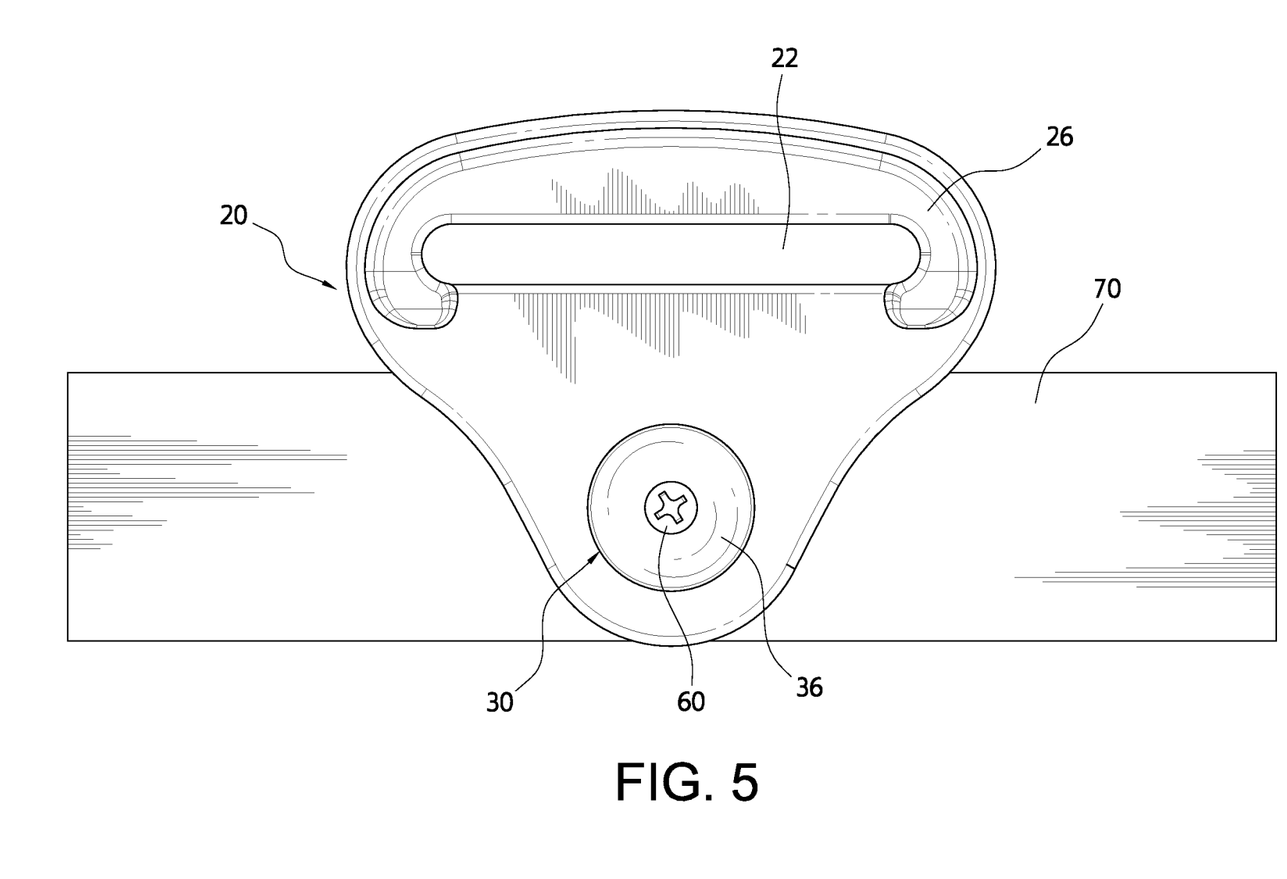
FIG. 5 is a top plan view of the strap tab assembly of FIG. 2.
Figure 6:
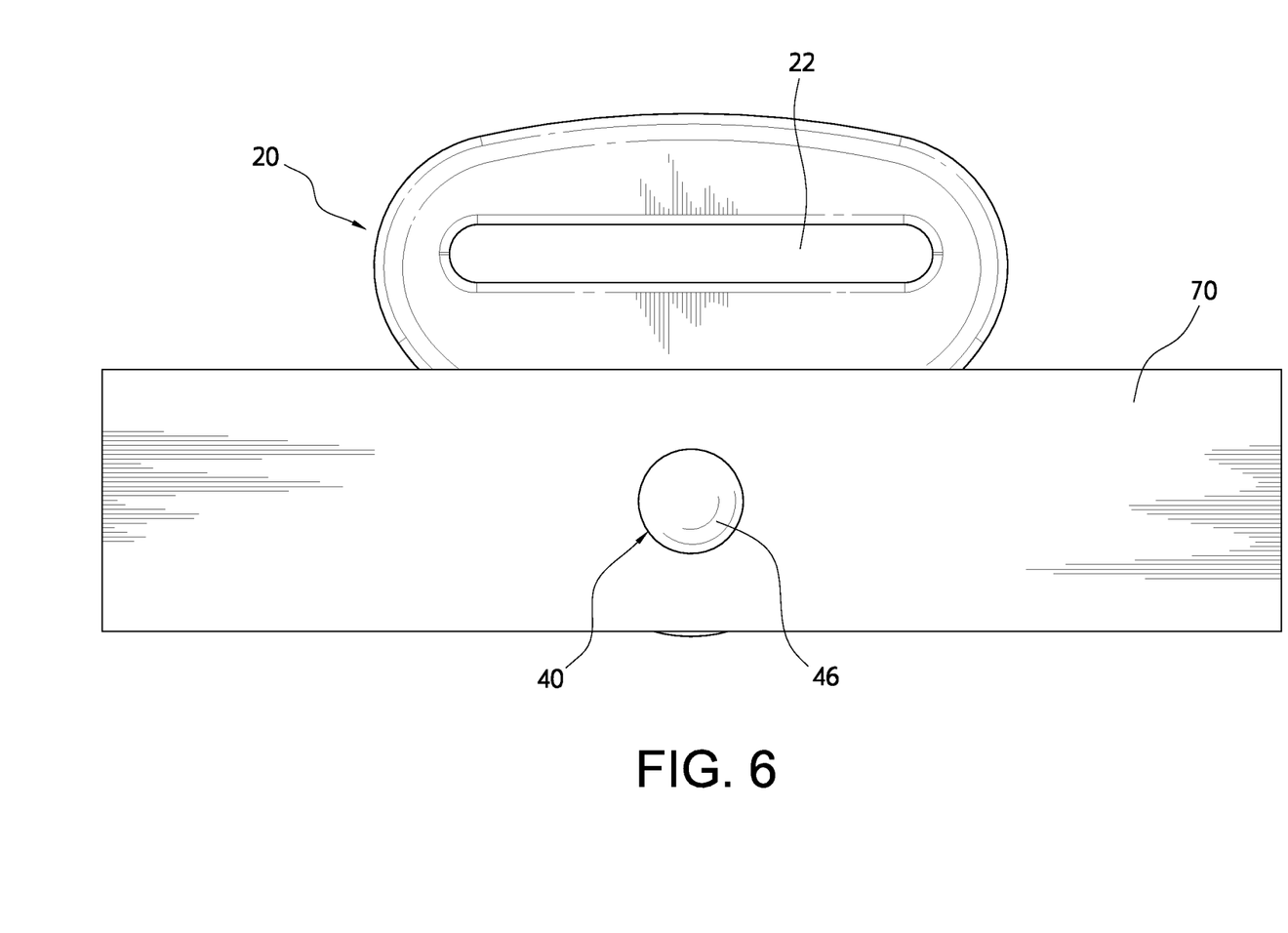
FIG. 6 is a bottom plan view of the strap tab assembly of FIG. 2.

As depicted in FIG. 3, the locking projection 34 is concentric with the top cover 36 and the female portion 38. The locking projection 34 protrudes outwardly beyond the circumference or periphery of the female portion 38 to allow the female portion 38 to extend freely through the locking hole 24 without interference, while the locking projection engages an inner periphery of the locking 24 due to their mating contour and dimensions. The female portion 38 corresponds in size and contour to the hole 72, but is size slightly smaller to permit free rotation of the strap tab 20 relative to the brace frame 70.

The locking projection 34 is configured to fittingly snap-lock into the locking hole 24 for securing the top cap 30 to the strap tab 20. Once secured, only the female portion 38 protrudes from the bottom surface of the strap tab 20, while only the top cover 36 abuts the top surface of the strap tab. The protruding female portion 38 is adapted to fit in a hole 72 on the brace frame 70 from either its internal or external surface. A bottom cap 40 with a square-shaped male portion 44 is adapted for being received in the center channel 32 of the female portion 38 from the opposite side of the brace frame 70 on which the strap tab 20 is located. It should also be appreciated that the corners of the square-shaped locking hole 24, the locking projection 34, and the male portion 44, may all be chamfered to allow for easy insertion.

The bottom cap 40 also comprises a low-profile convex bottom cover 46, and a fastener receiving cavity 42. A fastener 60, such as a self-tapping screw with a head 62 and a threaded body 64, can secure the top and bottom cap 30, 40 to the strap tab 20. The fastener 60 is inserted through the top cover 36 into the center channel 32 of the top cap 30, which also receives the male portion 44 of the bottom cap 40 at its opposite end. The threaded body 64 engages the fastener receiving cavity 42 of the bottom cap 40. The bottom cap 40 is preferably plastic so the fastener 60 can easily self-tap into the fastener receiving cavity 42. The length of the male portion 44 is determined based on the thickness of the brace frame to ensure there is enough thread engagement with the fastener 60 to secure the strap tab to a thick frame. Using a single fastener increases the ease with which a user can secure the strap tab to the brace.

The opening of the center channel 32 on the top cover 36 is smaller than the diameter of the center channel through the remainder of the top cap 30. This provides a stop for the head portion 62 of the fastener 60 to prevent it from entering further into the cavity 42. It also makes the top of the head portion 62 become substantially flush with the top surface of the top cap when the fastener is fully tightened. Such a configuration ensures that the fastener does not protrude from the top cap 30. This is important for maintaining a low profile on the brace so it does not contact the skin of a user or snag onto foreign objects when worn. This configuration also negates the need to place a protective cover or padding over either the top or bottom cap.

The axial alignment of the top and bottom cap 30, 40 with the fastener 60 allows the strap tab 20 to be fully rotational relative to the surface of the brace frame 70. It is advantageous to secure the locking projection 34 of the top cap 30 into the locking hole 24 of the strap tab 20 because when a user tightens the fastener 60, the strap tab 20 can be held in place so the entire strap tab assembly 19 does not rotate with the fastener. This greatly improves the ease and efficiency with which a user can service each strap tab in the field during use.

A circular washer 50 having a wave-like shape, such as a wave ring, is located between the bottom surface of the strap tab 20 and the brace frame 70 such that portions of the top and bottom caps 30, 40 that extend through the hole 72 in the brace frame also pass through the center of the washer. The presence of the washer 50 eliminates slack between the strap tab 20 and the brace frame 70 when the fastener 60 is tightened. The wave-like shape of the washer 50 distributes pressure caused from tightening the fastener 60 which helps resist loosening of the strap tab when rotated. This allows the strap tab 20 to easily and smoothly rotate as needed while also preventing it from unintentionally rotating freely without undue force. Without such a washer 50, overtightening the fastener 60 would make rotating the strap tab 20 much more difficult. The washer is preferably formed of a metallic material such as steel.

Figure 7:
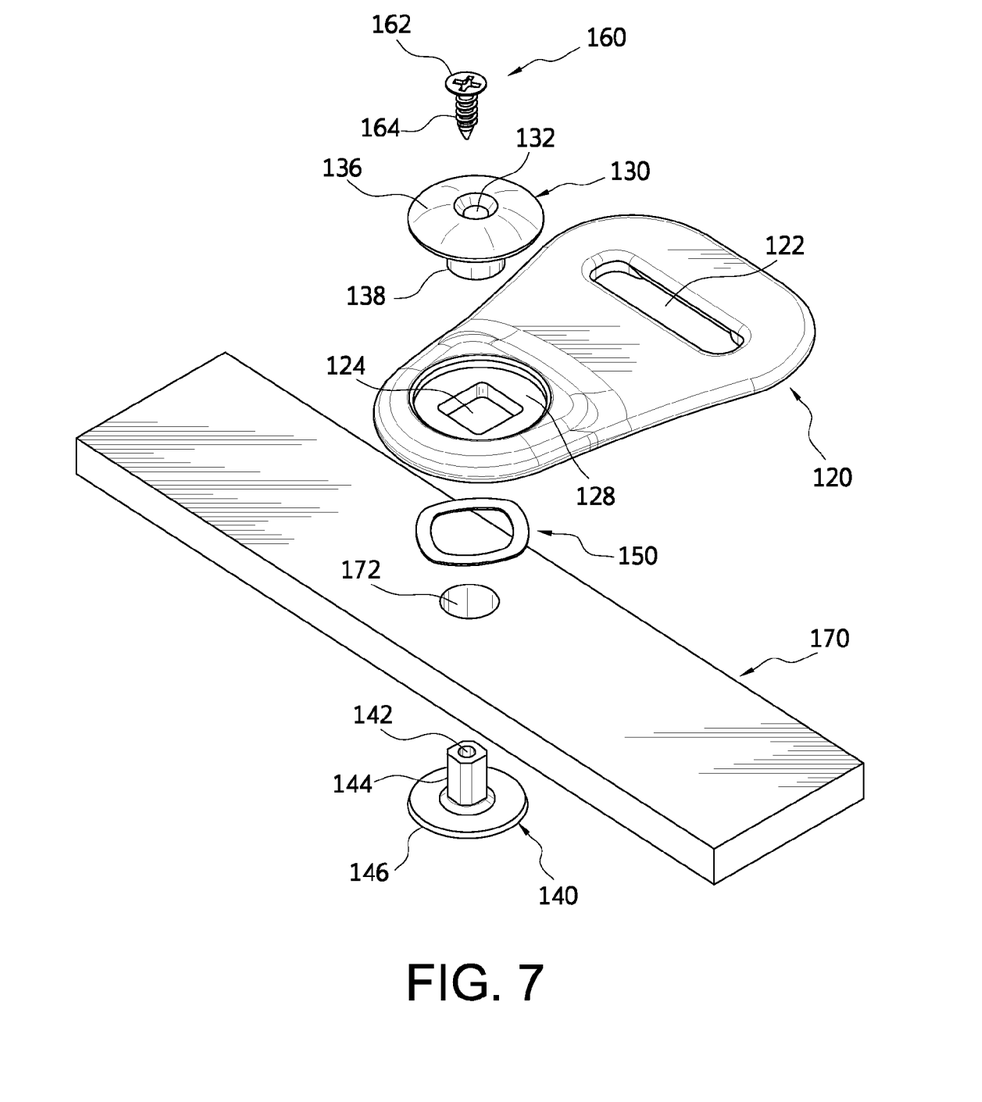
FIG. 7 is an exploded perspective view of another embodiment of the strap tab assembly according to the disclosure.
Figure 8:
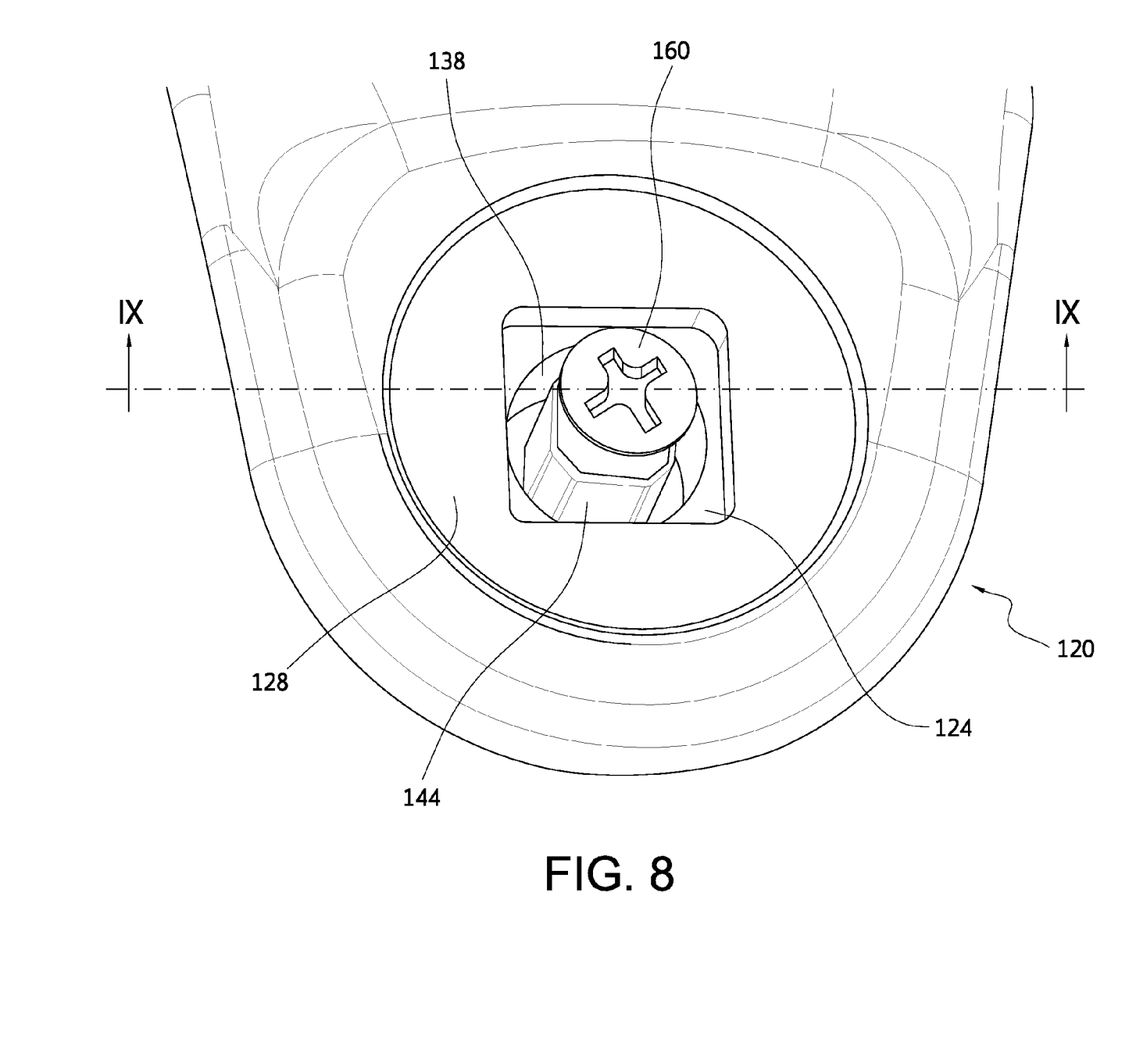
FIG. 8 is a detailed top plan view of the proximal end of the strap tab assembly of FIG. 7 without its top cap.
Figure 9:
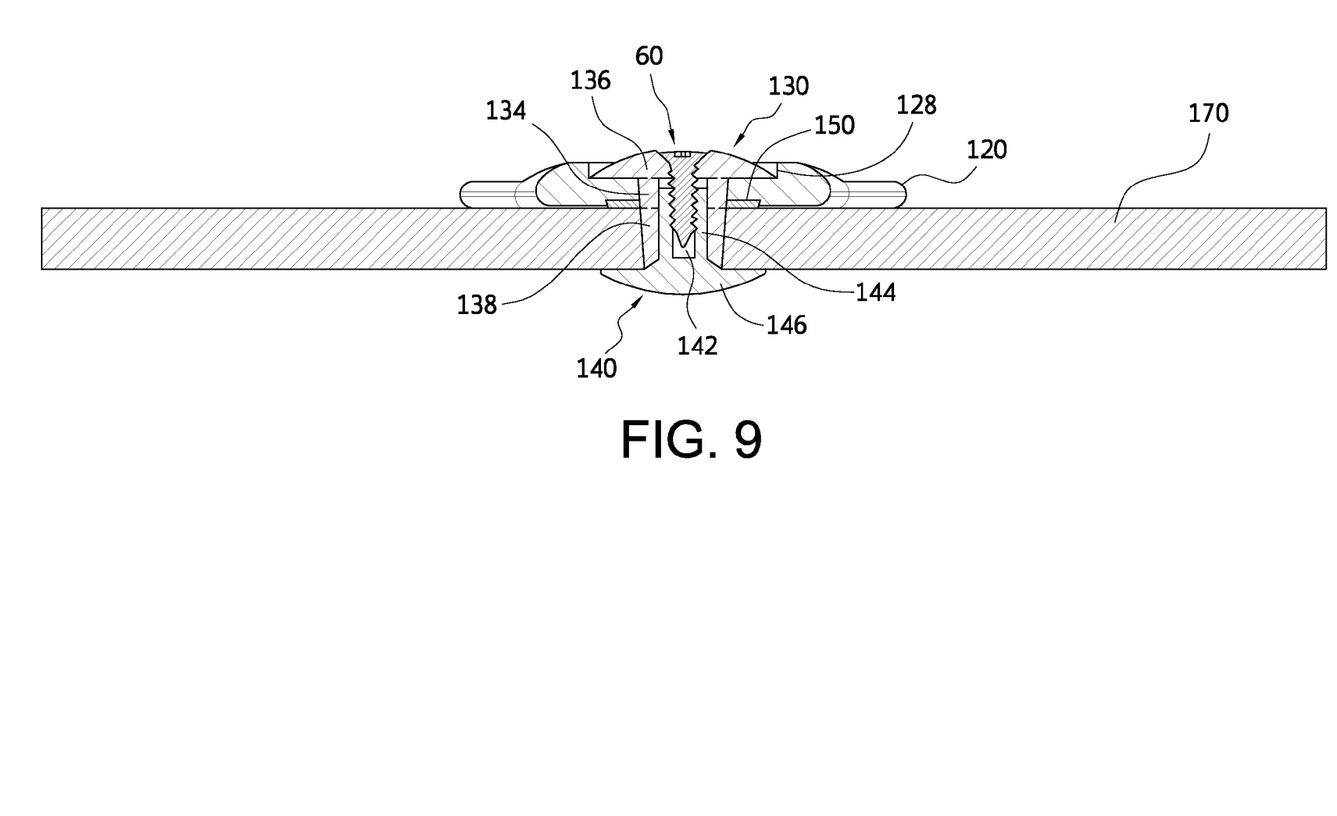
FIG. 9 a cross-sectional view taken along line IX-IX in FIG. 8.

Referring to FIGS. 7-9, another embodiment of the strap tab assembly is illustrated. The proximal end of the strap tab 120 includes a square-shaped locking hole 124 situated in the center of a recessed portion 126. The recessed portion 126 is adapted to receive the top cover 136 of the top cap 130. Referring to FIG. 9, a cross-sectional view of the strap tab assembly connected to a brace frame is shown. In this view, it can be seen that the recessed portion 126 permits the top cap 130 to lay substantially flush with the rest of the top surface of the strap tab. This arrangement helps maintain a low profile for the strap tab assembly since there are no outwardly extending protrusions that can easily snag a foreign object or irritate a user's skin.

The locking hole 124 allows the top cap 130 and the bottom cap 140 to engage each other for rotatably attaching the strap tab 120 to a hole 172 in the brace frame 170. The top cap 130 has a convex top cover 136 on one end and a female portion 138 with a substantially cylindrical exterior on the opposite end for engaging the hole 172. A square-shaped locking projection 134 corresponding to the locking hole 124 is on the top cap 130 between the top cover 136 and the female portion 138. A non-threaded center channel 132 with a generally square cross-section axially extends throughout both the female portion 138 and the locking projection 134.

The locking projection 134 is adapted to snap-lock into the locking hole 124 for securing the top cap 130 to the strap tab 120. Once secured, only the female portion 138 protrudes from the bottom surface of the strap tab 120, while only the top cover 136 abuts the top surface of the strap tab. The protruding female portion 138 is adapted to fit in a hole 172 on the brace frame 170 from either its internal or external surface. A bottom cap 140 with a generally square-shaped male portion 144 is adapted for being received in the center channel 132 of the female portion 138 from the opposite side of the brace frame 170 on which the strap tab 120 is located.

The bottom cap 140 also comprises a low-profile convex bottom cover 146, and a fastener receiving cavity 142. A fastener 160, such as a self-tapping screw with a head 162 and a threaded body 164, can secure the top and bottom cap 130,140 to the strap tab 120. The fastener 160 is inserted through the top cover 136 into the center channel 132 of the top cap 130, which also receives the male portion 144 of the bottom cap 140 at its opposite end. The threaded body 164 engages the fastener receiving cavity 142 of the bottom cap 140.

The axial alignment of the top and bottom cap 130,140 with the fastener 160 allows the strap tab 120 to be fully rotational relative to the surface of the brace frame 170. A circular washer 150 having a wave-like shape, such as a wave ring, is located between the bottom surface of the strap tab 120 and the brace frame 170 such that portions of the top and bottom caps 130,140 that extend through the hole 172 in the brace frame also pass through the center of the washer. The presence of the washer 150 eliminates slack between the strap tab 120 and the brace frame 170 when the fastener 160 is tightened.

Figure 10:
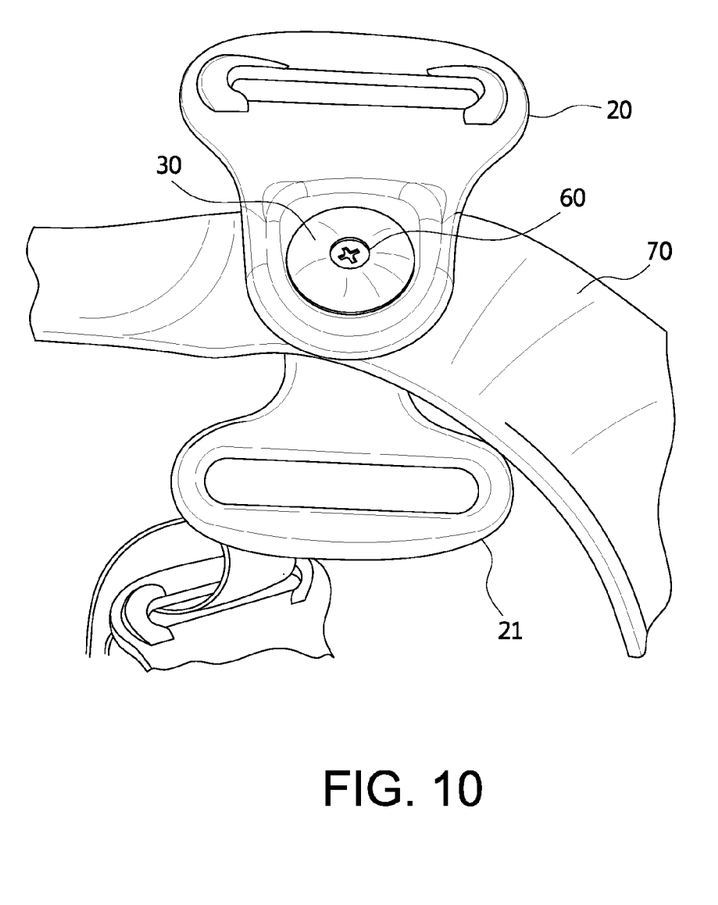
FIG. 10 is a top plan view of another embodiment of the strap tab assembly according to the disclosure.

Referring to FIG. 10, a strap tab is shown on either the internal or external surface of the brace frame and is secured to another corresponding strap tab on the opposite surface of the same frame. In this embodiment, a first strap tab 20 attaches to one side of the brace frame 70 and engages with the top cap 30 and a washer as described in regard to the embodiments of FIGS. 1-9. On the opposite side of the frame, a bottom cap 40 is secured to the first strap tab through a hole in the brace frame by a fastener 60 also according to the embodiments of FIGS. 1-9. A second strap tab 21 with a circular hole through its proximal end can be removably secured between the bottom cap 40 and the brace frame 70 by the engagement between the male portion 44 of the bottom cap and the fastener 60.

The circular hole of the second strap tab 21 is axially aligned with the hole of the frame and is enlarged such that it can freely rotate about the square-shaped cross-section of the male portion 44. The second strap tab 21 may also be provided with a circular recess at its proximal end for accommodating the bottom cover 46 of the bottom cap. Including such a recessed portion helps decrease the thickness of the strap tab to minimize its profile. In this embodiment, a single fastener 60 still secures the strap tabs to each other, and to the brace.

This configuration allows the strap tabs 20, 21 to be independently rotatable relative to both each other and the brace frame such that each corresponding strap better conforms to the shape of the user when the brace is worn. It also allows for extra straps to be used to better secure the brace to a user, or to provide a backup strap for the event that a first strap breaks. It should also be appreciated that a corresponding pair of strap tabs having differing shapes and sizes can be used on each side of the brace frame.

While the foregoing embodiments have been described and shown, alternatives and modifications of these embodiments, such as those suggested by others may be made to fall within the scope of the invention. While the hinge has been described in combination with a knee brace, it will be understood that the principles described may be extended to other types of orthopedic and prosthetic devices.

The invention claimed is:

1. A strap tab assembly, comprising:
   a strap tab defining a D-ring and forming a substantially square-shaped locking hole located generally at a proximal end, and an elongated slot on a distal end of the same strap tab opposite the proximal end and adapted for receiving a strap:
   a top cap defining a top cover, a square-shaped locking projection corresponding in shape to the locking hole, and a female portion forming a center channel and extending beyond and concentric with the locking projection, the locking projection located between the top cover and the female portion; and
   a bottom cap having a male portion adapted for being received in the center channel of the female portion, the bottom cap engaging and secured to the top cap by a fastener;
   wherein the locking projection extends beyond the periphery of the female portion, and is configured and dimensioned to correspond to and engage an inner periphery of the locking hole.

2. The strap tab assembly of claim 1, wherein the center channel axially extends through the female portion and the locking projection.

3. The strap tab assembly of claim 1, wherein the center channel defines a generally square-shaped profile, the male portion having a generally square-shaped profile configured and dimensioned to mate with the profile of the center channel.

4. The strap tab assembly of claim 3, wherein the male portion defines a threaded cavity concentric with the square-shaped profile thereof.

5. The strap tab assembly of claim 4, further comprising the fastener, the top cover defining a recess for receiving the fastener and communicating with the center channel, the fastener arranged to be seated within the recess and extend into the center channel to engage the threaded cavity and secure the top cap to the bottom cap.

6. The strap tab assembly of claim 5, wherein the fastener is arranged to be flush with the top cover when secured to the bottom cap.

7. The strap tab assembly of claim 1, wherein the top and bottom caps are substantially flat.

8. The strap tab assembly of claim 1, further comprising a washer located between the top and bottom caps, the washer having a central opening through which a cylindrical exterior of the female portion is extendable.

9. The strap tab assembly of claim 8, wherein the washer is a wave ring.

10. The strap tab assembly of claim 1, wherein the strap tab defines a recess concentric with the locking hole, the recess corresponding in shape to the top cover and the top cover is arranged flush against the strap tab within the recess.

11. The strap tab assembly of claim 1, further comprising the fastener securing the top cap to the bottom cap, the fastener rotatable independently relative to the top and bottom caps.

12. The strap tab assembly of claim 1, further comprising a frame element defining a hole through which a cylindrical exterior of the female portion extends and freely rotates within the hole.

* * * * *